US008275458B2

(12) United States Patent
Turcott

(10) Patent No.: US 8,275,458 B2
(45) Date of Patent: Sep. 25, 2012

(54) METHODS AND SYSTEMS FOR OPTIMIZING CARDIAC PACING INTERVALS FOR VARIOUS PHYSIOLOGIC FACTORS

(75) Inventor: Robert G. Turcott, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 162 days.

(21) Appl. No.: 12/790,456

(22) Filed: May 28, 2010

(65) Prior Publication Data

US 2010/0241186 A1    Sep. 23, 2010

Related U.S. Application Data

(60) Division of application No. 11/550,684, filed on Oct. 18, 2006, now Pat. No. 7,756,580, which is a division of application No. 10/816,629, filed on Apr. 1, 2004, now Pat. No. 7,130,689, which is a continuation-in-part of application No. 10/786,792, filed on Feb. 24, 2004, now abandoned.

(51) Int. Cl.
    *A61N 1/00* (2006.01)
(52) U.S. Cl. .......................................................... 607/27
(58) Field of Classification Search ...................... 607/27
    See application file for complete search history.

(56) References Cited

U.S. PATENT DOCUMENTS 4,688,573 A * 8/1987 Alt ................................. 607/21

* cited by examiner

*Primary Examiner* — George Manuel
(74) *Attorney, Agent, or Firm* — Steven M. Mitchell

(57) ABSTRACT

Methods and systems for performing pacing interval optimization are provided. One or more optimum pacing interval is determined for each of a plurality of different ranges of heart rate, different levels of autonomic tone, different body temperature ranges, or combinations thereof. The information (e.g., measures of hemodynamic response) collected to perform pacing interval optimization can be collected and stored in a table over disjoint periods of time. Such measures of hemodynamic performance are preferably relative measures, but can alternatively be absolute measures.

25 Claims, 12 Drawing Sheets

300

| Heart Rate | 141-150 |
| Heart Rate | 131-140 |
| Heart Rate | 121-130 |

312

| Heart Rate | 111-120 |
|---|---|
| Optimum PRV delay | 100 |
| Optimum AV delay | 113 |
| Optimum RV-LV delay | 13 |
| PRV100 - PRV60 | -105 |
| PRV100 - PRV120 | 33 |
| PRV100 - PRV150 | 71 |
| PRV100 - PRV180 | -13 |
| PRV100 - PRV210 | -57 |
| RARV113 - RARV103 | 10 |
| RARV113 - RARV73 | -22 |
| RARV113 - RARV123 | 5 |
| RARV113 - RARV133 | -32 |
| RARV113 - RARV153 | -45 |
| RVLV13 - RVLV73 | -63 |
| RVLV13 - RVLV53 | -21 |
| RVLV13 - RVLV-7 | 5 |
| RVLV13 - RVLV-17 | 7 |
| RVLV13 - RVLV | -37 |

| Body Position | Standing |
| Body Position | Sitting |

| Body Position | Recumbent |
|---|---|
| Optimum PRV delay | |
| Optimum AV delay | |
| Optimum RV-LV delay | |
| PRV100 - PRV60 | |
| PRV100 - PRV120 | |
| PRV100 - PRV150 | |
| PRV100 - PRV180 | |
| PRV100 - PRV210 | |
| RARV113 - RARV103 | |
| RARV113 - RARV73 | |
| RARV113 - RARV123 | |
| RARV113 - RARV133 | |
| RARV113 - RARV153 | |
| RVLV13 - RVLV73 | |
| RVLV13 - RVLV53 | |
| RVLV13 - RVLV-7 | |
| RVLV13 - RVLV-17 | |
| RVLV13 - RVLV | |

Fig. 6

METHODS AND SYSTEMS FOR OPTIMIZING CARDIAC PACING INTERVALS FOR VARIOUS PHYSIOLOGIC FACTORS

PRIORITY CLAIM

This application is a Divisional of and claims priority to U.S. patent application Ser. No. 11/550,684, filed Oct. 18, 2006 now U.S. Pat. No. 7,756,580, entitled METHODS AND SYSTEMS FOR OPTIMIZING CARDIAC PACING INTERVALS FOR VARIOUS PHYSIOLOGIC FACTORS; which is a Divisional of and claims priority to U.S. patent application Ser. No. 10/816,629, filed Apr. 1, 2004 now U.S. Pat. No. 7,130,689, entitled METHODS AND SYSTEMS FOR OPTIMIZING CARDIAC PACING INTERVALS FOR VARIOUS PHYSIOLOGIC FACTORS; which is a Continuation-In-Part of and claims priority to U.S. patent application Ser. No. 10/786,792, filed Feb. 24, 2004 now abandoned, entitled METHODS AND SYSTEMS FOR OPTIMIZING CARDIAC PACING INTERVALS DURING ELEVATE HEART RATES, which are incorporated herein by reference.

BACKGROUND OF THE INVENTION

1. Field of the Invention

The present invention relates generally to implantable cardiac stimulation devices. The present invention more particularly relates to methods and systems for performing pacing interval optimization.

2. Background Art

Implantable cardiac stimulation devices are well known in the art. Such devices may include, for example, implantable cardiac pacemakers and defibrillators either alone or combined in a common enclosure. The devices are generally implanted in a pectoral region of the chest beneath the skin of a patient within what is known as a subcutaneous pocket. The implantable devices generally function in association with one or more electrode carrying leads which are implanted within the heart. The electrodes are positioned within the heart for making electrical contact with the muscle tissue of their respective heart chamber. Conductors within the leads couple the electrodes to the device to enable the device to deliver the desired electrical therapy.

Traditionally, therapy delivery has been limited to the right side of the heart. However, new lead structures and methods have been produced and practiced for also delivering cardiac rhythm management therapy to the left heart. These lead structures and methods provide electrode electrical contact with the left atrium and left ventricle of the heart by lead implantation within the coronary sinus of the heart. As is well known, the coronary sinus passes closely adjacent the left atrium, extends into the great vein adjacent the left ventricle, and then continues adjacent the left ventricle towards the apex of the heart.

It has been demonstrated that electrodes placed in the coronary sinus and great vein may be used for left atrial pacing, left ventricular pacing, and cardioversion and defibrillation. These advancements enable implantable cardiac stimulation devices to address the needs of the wide patient population, from those that would benefit from right heart side pacing alone, to those that would benefit from left heart side pacing in conjunction with right heart side pacing (bi-chamber pacing), to those that would benefit from left heart side pacing alone.

Pacing interval optimization has been conventionally performed while a patient in a resting state. For example, a first test pacing interval (i.e., delay) is delivered for a period of three minutes and a measure of cardiac performance is obtained at the end of the period. The process is then repeated for each of several other test intervals (i.e., delays), and a best delay is derived from the ensemble of measurements. Algorithms are then used to hypothesize as to what pacing intervals should be used when the patient's heart rate is elevated. However, because the data used in such algorithms is obtained while the patient is at rest, the accuracy of such algorithms are limited. In other words, a calculated optimum pacing delay for an elevated heart rate, which was calculated based on measures obtained when the patient was at rest, may significantly differ from the actual optimum pacing delay at the elevated heart rate. Accordingly, it would be beneficial to provide improved methods and systems for determining optimum pacing intervals at elevated heart rates, and more generally, at different physiologic states.

A patient may experience an elevated heart rate for any number of reasons, such as physical exertion due to walking, jogging, or climbing stairs, emotional stress, or as part of the normal physiologic response to pain or infection. A possible reason that pacing interval optimization has been conventionally performed while a patient is in a resting state is because motion artifacts, e.g., resulting from patient motion, may corrupt measures of cardiac performance obtained while the patient's heart rate is elevated. Accordingly, it would be beneficial if the effects of motion artifacts could be minimized.

Conventionally, pacing interval optimization is performed in a clinic. Common current techniques include the use of echocardiography to maximize aortic flow or optimizing diastolic filling. However, such convention approaches are cumbersome, time-consuming, and expensive. Additionally, such approaches are highly sensitive to user skill, and therefore can be of marginal accuracy and precision. Additionally, conventional approaches are typically performed with the patient at rest in a supine or recumbent position, which is not representative of the preload, afterload, and autonomic status that is most common during daily activities. Finally, conventional pacing optimization using external measurement systems are necessarily limited to a single point in time, such as immediately following device implant or during periodic follow-up visits. The calculated optimum intervals in such settings thus do not track the changes in the true, underlying optima that can be expected with changes over time due to fluid status, posture, level of autonomic tone, and the like.

One specific approach, to optimization that is known in the art is often referred to as "gradient ascent". In one version of this approach, the hemodynamic response associated with a current pacing interval is compared to that induced by a test pacing interval. If the response improves, the current interval is replaced by the test interval. Otherwise, a different test interval is tried. This approach avoids retaining numerous measurements associated with a variety of test values which were obtained over an extended period of time. In theory, the device continuously evolves toward the best interval, and if the cardiovascular system is stable it should converge to the best value. However, the gradient ascent technique is only workable if the system is low in noise. When noise, measurement uncertainty, or variability in the underlying system is expected, the gradient ascent technique will typically fail to converge to a true optimum.

It would be beneficial to provide methods and systems for pacing interval optimization that overcomes some, and preferably all, of the above limitations.

BRIEF SUMMARY OF THE INVENTION

In accordance with embodiments of the present invention, pacing interval optimization is performed for various heart rates ranges, body positions, levels of autonomic tone, body temperature ranges, or combinations thereof.

In accordance with embodiments of the present invention, the pacing interval optimization is performed without interaction from a physician or technician (i.e., without human interaction). For example, there may be an optimal atrioventricular (RA-RV) delay and interventricular (RV-LV) delay for a heart rate between 61-70 beats per minute (bpm), a different optimal RA-RV delay and RV-LV delay for a heart rate between 71-80 bpm, 81-90 bpm, 91-100 bpm, etc. For another example, there may be an optimal RA-RV delay and RV-LV delay for a predominantly sympathetic autonomic tone and a different optimal RA-RV delay and RV-LV for a predominantly parasympathetic tone, etc.

In accordance with embodiments of the present invention, a sensor (e.g., an accelerometer) is used to detect whether significant motion is present, and measures of hemodynamic response (used for pacing interval optimization) are not obtained and/or stored while significant motion is present. The motion may be present, e.g., because the patient is climbing stairs, or in an aircraft in turbulent air. This aspect of the invention reduces the likelihood that motion artifacts will corrupt measures of cardiac performance (i.e., hemodynamic response measurements), which are used for pacing interval optimization calculations.

In accordance with an embodiment of the present invention, the data collected and used for pacing interval optimization can be collected over disjoint periods of time (i.e., the data need not be collected over a contiguous period of time). Conventionally, delivery of a first test pacing delay occurs for about 3 minutes, and then a second test pacing delay occurs for a following 3 minutes, and so on. Then an optimal pacing delay is derived from the measurements. In accordance with embodiments of the present invention, a lookup table is used to retain measures of hemodynamic performance (also referred to as cardiac performance measurements) for various heart rates, body positions, levels of autonomic tone, body temperature ranges, or combinations thereof. The data can be collected during disjoint periods of time. For example, if a patient just finished running, the patient's heart rate may be between 131-140 bpm for 20 seconds, then between 121-130 bpm for the next 30 seconds, and so on. In accordance with embodiments of the present invention, various pacing intervals are tested and the results (i.e., the corresponding hemodynamic responses) are stored in such a manner that the results can be combined with results from past and future times during which the patient's physiologic factors are similar. For a more specific example, during the 30 seconds that the patient's heart is between 131-140 bpm, three different pacing delays may be tested, and the results are stored. Then, the next time the patient's heart is within the same 131-140 bpm range, other delays are tested, so that an optimal delay can be determined. This can also be applied to body positions, levels of autonomic tone, temperature ranges, etc.

In accordance with embodiments of the present invention, relative cardiac (hemodynamic) performance measures are used, rather than absolute measures. For example, a device may pace at an RV-LV delay of 20 msec for 10 seconds, switch to an RV-LV delay of 40 msec for the next 10 seconds, and then calculate a relative hemodynamic response.

Further embodiments, and the features, aspects, and advantages of the present invention will become more apparent from the disclosure set forth below.

BRIEF DESCRIPTION OF THE FIGURES

FIG. 3 shows an exemplary lookup table, according to an embodiment of the present invention.

FIG. 6 shows an exemplary lookup table, according to another embodiment of the present invention that retains measures of cardiac performance for various body positions.

DETAILED DESCRIPTION OF THE INVENTION

The following description is of the best modes presently contemplated for practicing embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout.

Systems of the present invention can be implemented as part of an implantable stimulation device, such as the exemplary device described with reference to FIG. 1. Similarly, methods of the present invention can be performed by an implantable stimulation device, such as the stimulation device in FIG. 1. However, systems and methods of the present invention should not be limited to such implementation. For example, in accordance with some embodiments, certain portions of the inventive systems may be external to a stimulation device. Also, in accordance with some embodiments, certain steps of the inventive methods need not be performed by a stimulation device.

Exemplary Stimulation Device

Figure 1:
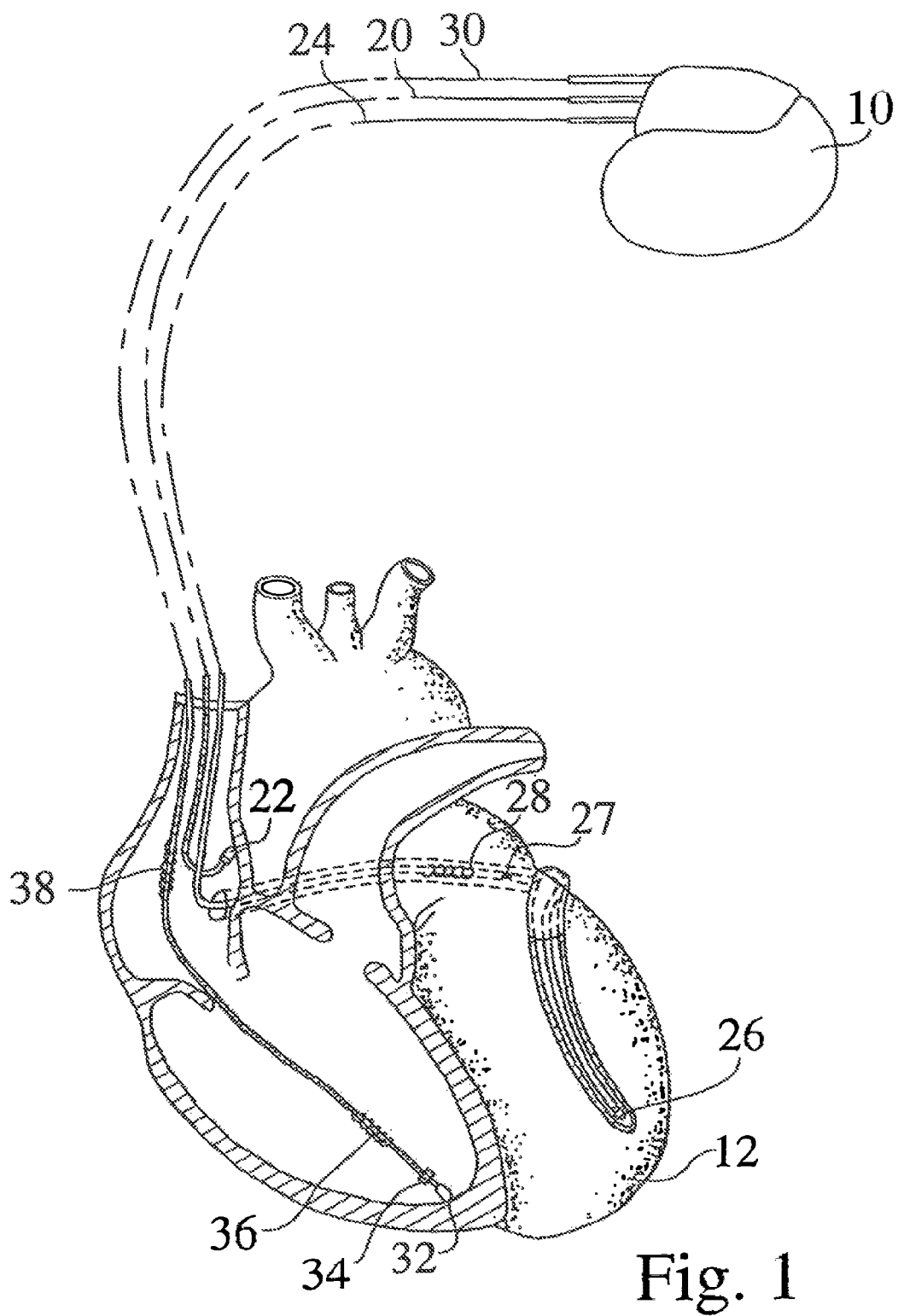
FIG. 1 is a simplified diagram illustrating an exemplary implantable stimulation device in electrical communication with at least three leads implanted into a patient's heart for delivering multi-chamber stimulation and shock therapy.

As shown in FIG. 1, there is an exemplary stimulation device 10 (also referred to as a pacing device, or a pacing apparatus) in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 2:
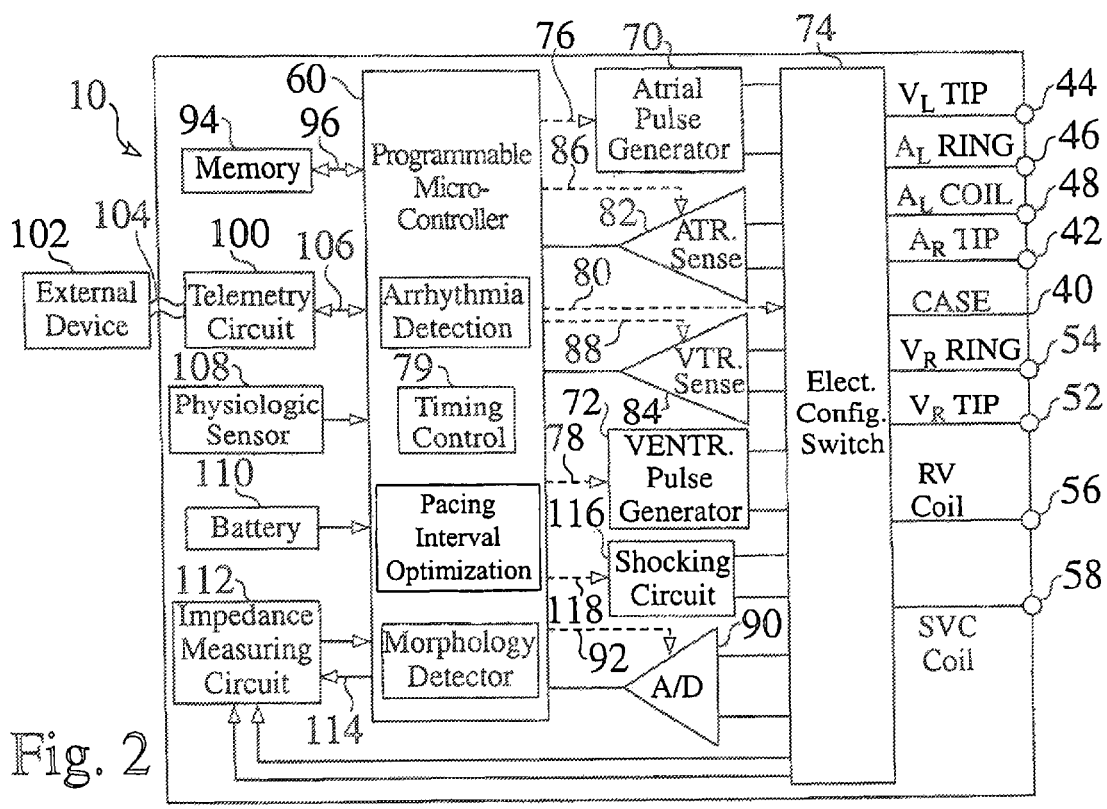
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art. In specific embodiment of the present invention, the microcontroller 60 performs some or all of the steps associated with determining optimal pacing parameters in accordance with the present invention.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the stimulation device and their inter-relationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control pacing parameters (e.g., the timing of stimulation pulses) as well as to keep track of the timing of refractory periods, PVARP intervals, noise detection windows, evoked response windows, alert intervals, marker channel timing, etc., which is well known in the art. Examples of pacing parameters include, but are not limited to pacing rate and pacing intervals, such as atrio-ventricular (RA-RV) delay, interventricular (RV-LV) delay, interatrial (RA-LA) delay and intraventricular ($RV_1$-$RV_2$ or $LV_1$-$LV_2$) delay.

The switch bank 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Such sensing circuits, 82 and 84, can be used measure the hemodynamic responses that result from the various pacing intervals that are tested in accordance with embodiments of the present invention.

The outputs of the atrial and ventricular sensing circuits, 82 and 84, are connected to the microcontroller 60 which, in turn, are able to trigger or inhibit the atrial and ventricular pulse generators; 70 and 72, respectively, in a demand fashion in response to the absence or presence of cardiac activity, in the appropriate chambers of the heart. The sensing circuits, 82 and 84, in turn, receive control signals over signal lines, 86 and 88, from the microcontroller 60 for purposes of measuring hemodynamic response at appropriate times, and for controlling the gain, threshold, polarization charge removal circuitry (not shown), and timing of any blocking circuitry (not shown) coupled to the inputs of the sensing circuits, 82 and 86.

For arrhythmia detection, the device 10 utilizes the atrial and ventricular sensing circuits, 82 and 84, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 can be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

A feature of the present invention is the ability to sense and store a relatively large amount of data. Such data can then be used for subsequent analysis to guide the programming of the device and/or to appropriately adjust pacing parameters in accordance with embodiments of the present invention.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to an external device 102 through an established communication link 104.

For examples of such devices, see U.S. Pat. No. 4,809,697, entitled "Interactive Programming and Diagnostic System for use with Implantable Pacemaker" (Causey, III. et al.); U.S. Pat. No. 4,944,299, entitled "High Speed Digital Telemetry System for Implantable Device" (Silvian); and U.S. patent application Ser. No. 09/223,422, filed Dec. 30, 1998, entitled "Efficient Generation of Sensing Signals in an Implantable Medical Device such as a Pacemaker or ICD" (note: this relates to transfer of EGM data) (McClure et al.), which patents are hereby incorporated herein by reference.

In the preferred embodiment, the stimulation device 10 further includes one or more physiologic sensor 108, that can be used to measure hemodynamic responses, and thus, used to detect changes in cardiac performance or changes in the physiological condition of the heart. A single measure of hemodynamic response can be measured for each pacing interval that is tested, or multiple measures can be obtained and optionally combined into a single measure.

The microcontroller 60 can adjust the various pacing parameters (such as rate, P-RV Delay, RA-RV Delay, RV-LV Delay, $RV_1$-$RV_2$ Delay, etc.) in accordance with the embodiments of the present invention. The microcontroller 60 controls adjustments of pacing parameters by, for example, controlling the stimulation pulses generated by the atrial and ventricular pulse generators, 70 and 72. While shown as being included within the stimulation device 10, it is to be understood that the physiologic sensor 108 may also be external to the stimulation device 10, yet still be implanted within the patient. For example, the sensor 108 can be located inside the device 10, on the surface of the device 10, in a header of the device 10, or on a lead (which can be placed inside or outside the bloodstream). A sensor may even be non-implantable, and communicate by telemetry with the microcontroller 60. For example, a sensor can be implemented in a finger cuff, a wristband, a configuration resembling a watch, or a configuration resembling a clip-on earring.

The physiologic sensor 108 can include a light source and light detector, which can be used to produce a plethysmography signal, from which hemodynamic measures can be obtained. Additional details of such sensors are described in U.S. Pat. No. 6,591,639 (Turcott) and U.S. Pat. No. 6,409,675 (Turcott), each of which is incorporated by reference herein. As described in these patents, a plethysmography signal can be used to measure vascular volume, which is an indicator of hemodynamic status. Such sensors can also be used to measure oxygen saturation, which is another indicator of hemodynamic status. Another example of a physiologic sensor is a microphone sensor or an accelerometer, which can be used to measure heart sounds, as is also explained in the '639 and '675 patents. Additional examples of physiologic sensors include, but are not limited to, a pressure transducer, a strain gauge, a Doppler flow sensor, an impedance sensor, and an ultrasound transducer. Embodiments of the present invention should not be limited to the specific type of transducer(s) used to measure hemodynamic performance, or the specific measures of hemodynamic performance (e.g., blood oxygen saturation, pulse amplitude, pulse amplitude variability, pulse pressure, arterial volume, autonomic tone, atrial cycle length, ventricular cycle length, intracardiac impedance, etc.).

The stimulation device 10 additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown only for completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5-10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognize), and pertaining exclusively to the treatment of fibrillation. Accordingly, the microcontroller 60 is capable of controlling the synchronous or asynchronous delivery of the shocking pulses.

Exemplary Lookup Table

In accordance with embodiments of the present invention, a lookup table is used to retain cardiac performance measurements (also known as hemodynamic response or performance measurements) for various heart rates, with the data potentially collected during disjoint periods of time. For example, if a patient just finished running, his heart rate may be between 131-140 bpm for 60 seconds, then between 121-130 bpm for the next 30 seconds, and so on. In the present invention, the hemodynamic response data that is used to perform pacing interval optimization is recorded in such a manner that the most recently obtained data can be combined with data from past and/or future times during which the patient's heart rate is within the same ranges. For a more specific example, during the 60 seconds that the patient's heart rate is between 131-140 bpm, assume that three different pacing intervals are tested, and the results (i.e., data) are stored. Then, the next time the patient's heart is within the same 131-140 bpm range, other intervals (i.e., delays) are tested, so that an optimal delay can be determined. FIG. 3 shows an exemplary lookup table 300, according to an embodiment of the present invention. Such a lookup table is preferably stored in the memory 94 of the implantable stimulation device 10.

In FIG. 3, the portion of the lookup table 300 shown in detail corresponds to a heart rate between 111-120 bpm. The table includes previously determined optimum pacing intervals, along with previously determined relative measures of cardiac performance. More specifically, in FIG. 3, the previously determined optimum P-RV (atrial sense; RV pace) delay is shown to be 100 msec, the previously determined optimum RA-RV (RA pace; RV pace) delay is shown to be 113 msec, and the previously determined optimum RV-LV (RV pace; LV pace) delay is shown to be 13 msec. For the additional rows in the exemplary table: in the first column the first value represents a baseline pacing interval and the second value represents a test pacing interval; and the value in the second column indicates a relative change in cardiac performance (with a positive number representing an increase in performance, and a negative number representing a decrease in performance). For example, in row 312, "PRV100-PRV60" indicates that a baseline P-RV delay is 100 msec, and a test P-RV delay is 60 msec. In the same row 312, the "−105" indicates that a change from the baseline P-RV delay (100 msec) to the test P-RV delay (60 msec) caused a relatively large decrease in cardiac performance.

A relative cardiac performance value (e.g., −105) can been calculated, for example, after the hemodynamic response was measured while the heart was paced using a baseline interval (e.g., a P-RV delay of 100 msec) for a period of time (e.g., 10 seconds), and then paced using a test interval (e.g., a P-RV delay of 60 msec) for a following period of time (e.g., the following 10 seconds). Since the cardiac performance values stored in the table are relative values, there is no need for units. Rather, magnitude and sign (i.e., + or −) provide enough information. However, absolute measures of cardiac performance can be obtained and stored, if desired. Where absolute measures are used, it is not necessary to use baseline pacing intervals, since the absolute measures can be compared directly to one another.

Similar data is also stored for other heart rates that are likely to be encountered. For example, other heart rate ranges may include 121-130 bpm, 131-140 bpm and 141-150 bpm, etc., as shown in FIG. 3. Of course there are many other heart rate ranges that will likely be included in the lookup table. Also, the ranges used in the lookup table can have greater or less granularity than is shown in the exemplary table 300. An extreme case occurs when all possible heart rates are lumped together in the same range. In this case no distinction is made with respect to heart rate, however the techniques of monitoring for motion and/or performing analysis over noncontiguous (disjoint) periods of time can still be employed to avoid degradation by motion artifact. Additionally, there can be many more test pacing intervals than shown in the exemplary table 300. The test pacing intervals can be constant, random, evolutionary, etc. Also, there can be many more entries retained for each test pacing interval. For example, adding another column to exemplary table 300 would allow the most recent and the next most recent measurements to be retained.

In the exemplary table 300, the previously determined optimum pacing intervals were used as the baseline pacing intervals. This makes it easy to determine whether a test pacing interval provides better or worse cardiac performance than a previously determine optimum pacing interval. However, the baseline need not be the previously determined optimum pacing intervals.

The table 300 shown in FIG. 3 is just one example of how a lookup table could be organized. Other variations are also within the spirit and scope of the present invention.

Pacing Interval Optimization at Elevated Heart Rates

Figure 4:
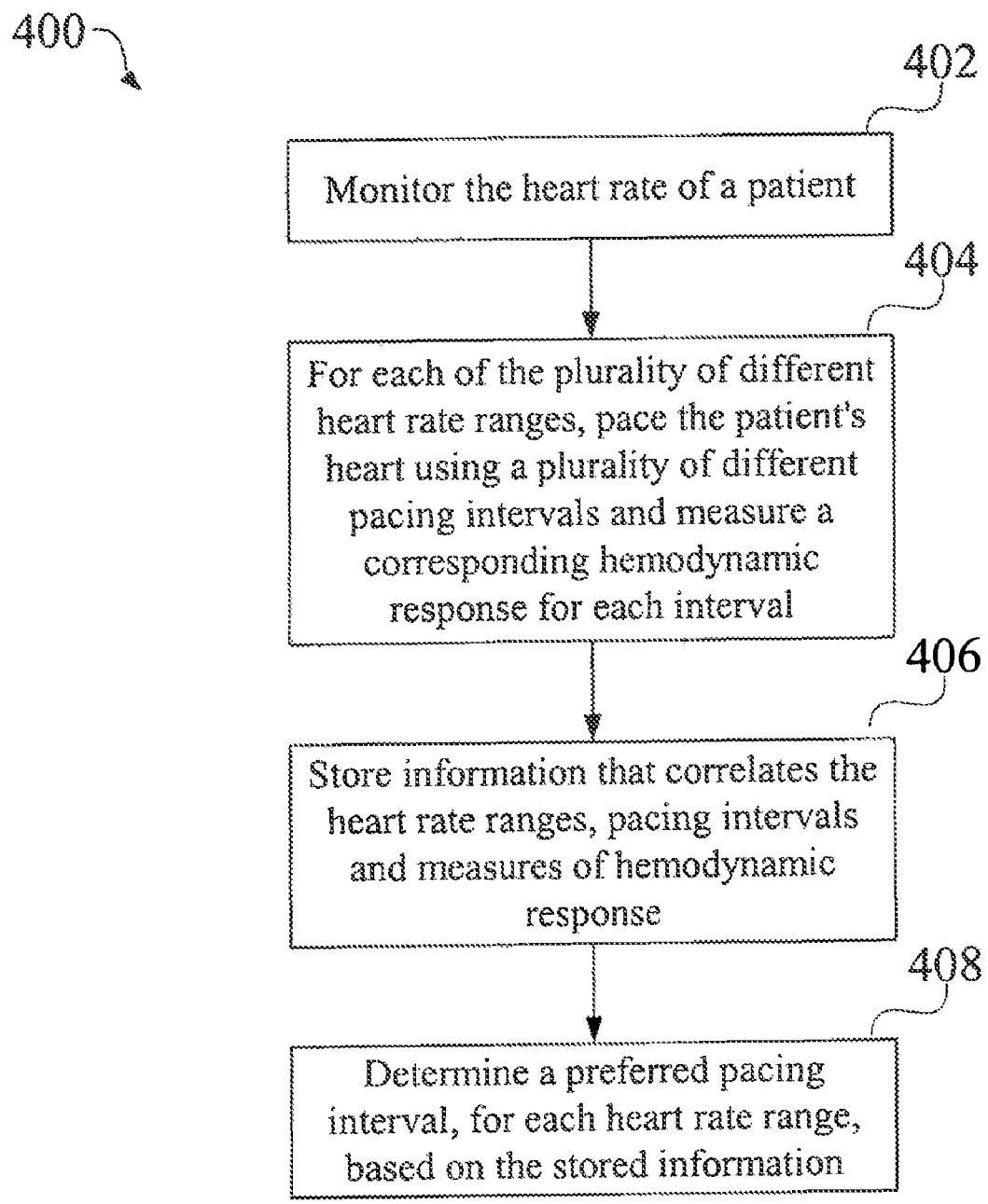
FIG. 4 is a high level flow diagram useful for describing how pacing interval optimization can be performed at elevated heart rates, in accordance with embodiments of the present invention.

The high level flow diagram 400 shown in FIG. 4 will now be used to explain how automatic pacing interval optimization can be performed at elevated heart rates, in accordance with embodiments of the present invention. The steps of flow diagram 400 are preferably performed by an implanted device, without any interaction from a physician or technician (i.e., without human interaction). As shown in FIG. 4, a patient's heart rate is monitored, at step 402. Depending on the pacing being performed, the monitored heart rate may be an intrinsic sinus rate, if a stimulation device (e.g., stimulation device 10) is in a tracking mode, or the monitored heart rate may be a paced rate, if the stimulation device is in a pacing mode. Referring back to FIG. 2, for example, the atrial sensing circuits 82 and/or ventricular sensing circuits 84 along with the microcontroller 60 can be used to monitor a patient's heart rate.

As specified at step 404, for each of a plurality of different heart rate ranges, the patient's heart is paced using a plurality of different pacing intervals, and a corresponding hemodynamic response is measured for each pacing interval. The plurality of different pacing intervals used for pacing can be the same for each heart rate range, or may differ for different heart rate ranges. The heart rate ranges can include, for example, 61-70 bpm, 71-80 bpm, 81-90 bpm, 91-100 bpm, 101-110 bpm, 111-120 bpm, etc.

The pacing intervals can define, e.g., atrioventricular (P-RV or RA-RV) delays. The pacing intervals can alternatively, or additionally, define, interventricular (RV-LV) delays, interatrial (RA-LA) delays, intraventricular ($RV_1$-$RV_2$ or $LV_1$-$LV_2$) delays, etc. The initiating event, from which the interval/delay is specified, can be either a delivered pace pulse, or a sensed depolarization. The term P-RV delay is used herein to refer to a sensed atrial event and a paced ventricular event (P taken from its use in reference to atrial depolarization in standard ECG terminology). These are just a few examples, which are not meant to limit the scope of the present invention.

The information obtained at step 404 is stored (e.g., in memory 94 of stimulation device 10), as indicated at step 406. More specifically, step 406 includes storing information that correlates the heart rate ranges, pacing intervals and measured hemodynamic responses. The information stored at step 406, is used at step 408, to select a preferred pacing interval (or preferred pacing intervals) for each heart rate range. For example, the pacing interval producing the best hemodynamic response (relative or absolute) for a given heart rate range, can be selected as the optimum pacing interval for that range. Alternatively, the stored information can be used to predict an optimum pacing interval for that range (e.g., using a curve fitting algorithm, or the like).

Preferably, a plurality of test pacing intervals (e.g., a plurality of RV-LV delays) and corresponding hemodynamic response values are stored for each heart rate range. By determining an optimum pacing interval from an ensemble of stored test intervals, greater accuracy and precision can be achieved. For example, a continuous curve can be fit to the stored data, as just mentioned. If the number of degrees of freedom of the curve is smaller than the number of test intervals, then effective averaging can be performed both at individual test intervals and across the range of test intervals. This approach is particularly desirable in optimization that occurs at elevated heart rates, since elevated heart rates can be expected to change with time rather than remain stable. For these and other reasons, it is believed that embodiments of the present invention will provide better pacing interval optimization than is achieved by conventional gradient ascent techniques. More specifically, because the degree of expected variability and noise is high, it is believed that a gradient ascent technique for determining optimum pacing intervals would converge very slowly to optimum values.

Assume, for example, that there are five different pacing intervals (e.g., RA-RV delays) to test for each heart rate range, and that it takes 20 seconds to obtain enough information to determine a relative hemodynamic response for a test pacing interval. This may include, for example, pacing for 10 seconds at a baseline, followed by pacing for 10 seconds at the test interval. Using these assumptions, it would take 100 seconds (i.e., 5×20 second=100 seconds) to pace at the five different pacing intervals and produce corresponding relative hemodynamic response measures. This presents a challenge, since it is unlikely that the patient's heart rate will be within each of the various heart rate ranges continuously for 100 seconds. To overcome this, in accordance with embodiments of the present invention, the pacing using the plurality of different pacing intervals can occur over noncontiguous (i.e., disjoint) periods of time. For example, if the patient just finished running, his heart rate may be between 131-140 bpm for 40 seconds, then between 121-130 bpm for the next 60 seconds, and so on. Using embodiments of the present invention, this may be enough time for: relative hemodynamic response measures to be obtained for only two of the five test intervals during the 40 seconds that the patient's heart rate is. between 131-140 bpm; and relative hemodynamic response measures to be obtained for only three of the five test intervals during the 60 seconds that the patient's heart rate is between 121-130 bpm. This information is stored in a lookup table (e.g., as described with reference to FIG. 3). Then, the next time the patient's heart rate is between 131-140 bpm, some or all of the remaining test intervals can be used for pacing, and corresponding hemodynamic response measures can be obtained and stored. Similarly, the next time the patient's heart rate is between 121-130 bpm, some or all of the remaining test intervals can be used for pacing, and corresponding hemodynamic response measures can be obtained and stored. In this manner, the lookup table can be populated and updated over time.

As was explained above, one or more optimum pacing interval can be stored for each heart rate range. For example, as shown in FIG. 3, an optimum P-RV delay, RA-RV delay, and RV-LV delay can be stored for each heart rate range. The term "optimum pacing interval," as used herein, refers to a best or preferred pacing interval that is determined based on currently available information. It is possible (and likely) that there are pacing intervals that will provide better cardiac performance than the most recently determined optimum pacing intervals. Thus, the term "optimum" does not necessary refer to an absolute best pacing interval. Rather, the term "optimum" refers to a pacing interval that is (or is predicted to be) the best, based on the limited information currently available.

Optimum pacing intervals can be updated periodically, e.g., once a day, once every few hours, after a change in position or posture, etc. In another embodiment, a new optimum pacing interval is determined each time a new hemodynamic response measure is stored. In a further embodiment, a new optimum pacing interval is determined after a new hemodynamic response measure has been determined for each of a predefined group of test intervals. Of course, other variations are also possible.

In accordance with an embodiment of the present invention, a previously determined optimum pacing interval is replaced with a new interval that corresponded to an improved hemodynamic response. In another embodiment, the new interval that corresponds to an improved hemodynamic response is used to form a running average with previously stored optimum pacing intervals. In still another embodiment, the new interval that corresponds to an improvement in hemodynamic response is combined with the previously stored value, e.g., using a weighted sum calculation. Of course, other variations are also possible.

As mentioned above, hear rate monitoring, pacing, measuring of hemodynamic response, and selection of preferred pacing intervals, in accordance with embodiments of the present invention, are preferably automatically performed by an implantable device without interaction from a physician or technician. Such systems provide pacing optimization less expensively than convention devices that require human interaction, since physician or technician involvement is not necessary, and use of clinic time, space, and resources are avoided. Furthermore, embodiments of the present invention provide for frequent or semi-continuous optimization multiple times a day. In addition to being used to increase pacing optimization accuracy, embodiments of the present invention also track changes in underlying optimum pacing intervals that may occur with time and physiologic state.

Minimizing the Effects of Motion Artifacts

In accordance with embodiments of the present invention, one or more sensor is used to detect motion, and certain steps of the present invention are not performed when significant motion is present. In this manner, the effects of motion artifacts on measures of hemodynamic performance are reduced, and hopefully eliminated. Such features shall now be summarized with reference to the high level flow diagram 500 of FIG. 5. The steps in flow diagram 500 can be performed while a patient's heart is being paced using a plurality of different pacing intervals. The pacing can be performed while the patient is at rest (i.e., while the patient's heart rate is relatively stable). Preferably, however, the pacing is performed as the patient's heart rate moves through various heart rate ranges, as was described above.

Figure 5:
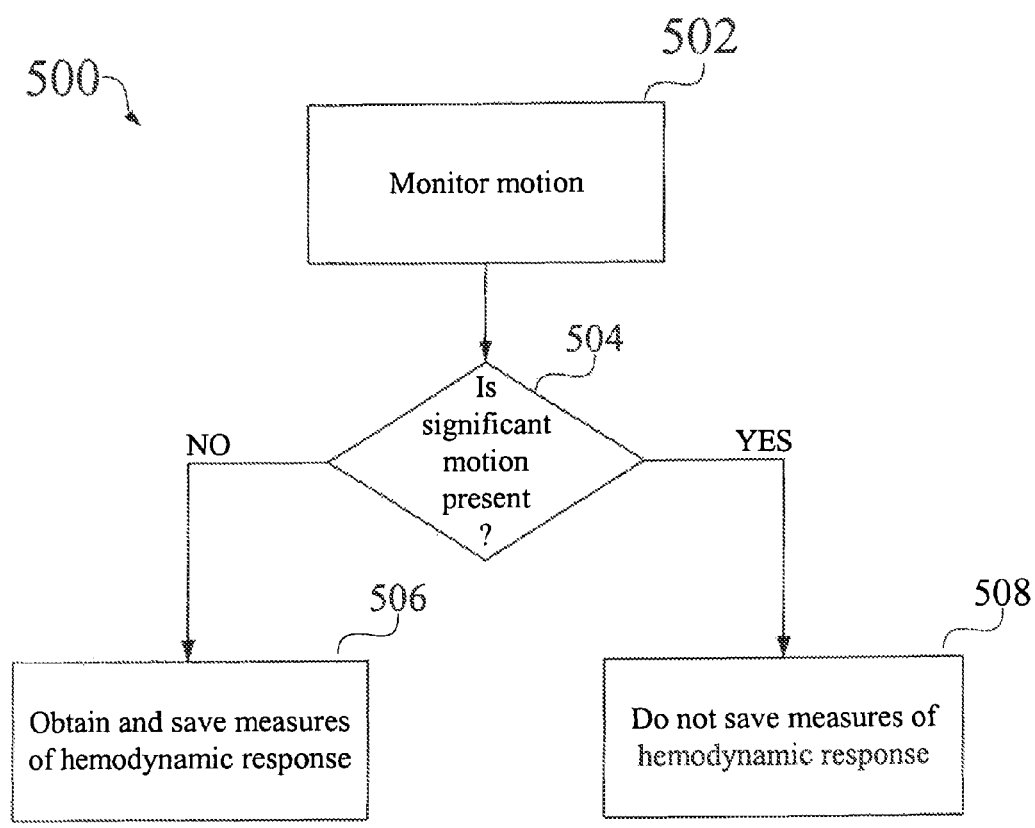
FIG. 5 is a high level flow diagram useful for describing how effects of motion artifacts, on measures of hemodynamic response, can be reduced and hopefully eliminated.

Referring to FIG. 5, at step 502, motion that may effect measures of hemodynamic response is monitored. A sensor, such as an accelerometer, can be used to monitor motion. Such a sensor can be part of the implantable stimulation device (e.g., device 10) used to perform pacing. In other words, the sensor can be, e.g., located in, on or adjacent the housing 40 of the device 10, or on a lead extending from the stimulation device 10. Alternatively, analysis of the output of the hemodynamic sensor is performed to detect motion artifact. This intrinsic analysis avoids the need for a separate sensor.

At step 504, there is a determination of whether significant motion is present. Step 504 is likely performed by comparing sensor measurements to a threshold. In such an embodiment, it is presumed that significant motion is not present when sensor measurements do not exceed the threshold, and that significant motion is present when sensor measurements exceed the threshold. The threshold can be predefined. Alternatively, the threshold can be programmable, and may even be dynamically adjusted, depending on implementation. In another embodiment intrinsic analysis of the output of the hemodynamic sensor is performed to detect motion artifacts. For example, in the absence of motion, well defined arterial pulsations are expected in an arterial pressure sensor or a photoplethysmography sensor, either of which can be used for measuring hemodynamic response. Template matching can be performed to verify that the pulsations due to cardiac systole are present. An inability to detect the presence of these pulsations indicates that motion artifact is significant.

Based on the assumption that motion artifacts will corrupt measures of hemodynamic response, the determinations of whether significant motion is present at step 504, are used to determine whether or not to store measures of homodynamic response, which are used for pacing interval optimization. More generally, as specified at step 506, while significant motion is not present, hemodynamic response measurements are made and stored (i.e., pacing interval optimization steps are performed). However, while significant motion is present, measures of hemodynamic response are not stored, as specified at step 508. For example, in accordance with an embodiment of the present invention, measures of cardiac performance are not made (and thus, there are no measures to store) when significant motion is detected. Alternatively, measures of cardiac performance are made, but are not stored (i.e., saved) when significant motion is detected. In accordance with a specific embodiment of the present invention, the previously determined optimal pacing parameter(s) is/are used for pacing, when significant motion is present, and test pacing intervals are not used until significant motion is not present. These features of the present invention reduce the likelihood that motion artifacts will corrupt measures of cardiac performance (i.e., hemodynamic response measurements), which are used to perform the pacing interval optimization calculations.

The measures of hemodynamic performance that are obtained and stored are preferably relative measures, but can be absolute measures, as was explained in detail above. Further, if multiple hemodynamic performance measures (each associated with a different pacing interval) are to be obtained for each of a plurality of different heart rate ranges, the measures corresponding to a specific heart rate range can be obtained over disjoint periods of time, as was explained in detail above.

Pacing Interval Optimization for Various Body Positions

In the same way that a lookup table can be used to retain different optimum pacing interval settings for different heart rates, different optimum settings and raw data can also be retained based on other physiologic factors that are likely to influence optimum pacing interval parameters. For example, cardiac contractility is well known to depend on the amount of preload, i.e., the amount of blood volume that fills the chambers before contraction. Preload depends on the rate of return of blood from the periphery, which is strongly influenced by posture. In particular, the amount of preload varies greatly when a patient moves from a recumbent (i.e., lying) position, to sitting, and to standing. These changes in posture can be readily detected, e.g., by a DC-coupled 3-dimensional accelerometer as described in U.S. Pat. No. 6,658,292, a multi-axis DC accelerometer as described in U.S. Pat. No. 6,466,821, or an external field sensor as described in U.S. Pat. No. 6,625,493, each of which are incorporated herein by reference. Such sensors are able to distinguish among different static positions. In addition, since the sensors can detect motion, they can be used to distinguish between a static vertical position, such as sitting, and a standing position, which due to the dynamics of balance is associated with subtle motion that is not present while sitting. In this way an implantable pacemaker, using one of the above mentioned sensors or other sensing modality, can detect a change in body position (i.e., posture), and switch pacing parameters to the optimal values that have previously been determined for that body position. In addition, it can update hemodynamic response measurements and estimates of optimum parameters, in exact analogy with heart rate as was described above. In practice, the pacemaker may operate by retaining data for each of a range of heart rates without regard to body position, or it may operate by retaining data for each of a variety of body positions without regard to heart rate, or its may incorporate both, so that a unique set of data is stored for each combination of body position and range of heart rates. This approach can of also be extended to other factors which may influence optimum parameter settings, such as autonomic tone or body temperature, as will be described in more detail below.

FIG. 6 shows an exemplary portion of a lookup table 600, which is similar to the lookup table 300 of FIG. 3, except that instead of retaining cardiac performance measures for various heart rates, the cardiac performance measures are retained for various body positions. For ease of illustration, table 600 is not populated with hemodynamic performance data. As with table 300, the data in table 600 can be collected during disjoint periods of time. For example, a patient may be sitting for 60 seconds, and then change to a standing position. In the present invention, the hemodynamic response data that is used to perform pacing interval optimization is recorded in such a manner that the most recently obtained data can be combined with data from past and/or future times during which the patient has the same body position. For a more specific example, during the 60 seconds that the patient is sitting, assume that three different pacing intervals are tested, and the results (i.e., data) are stored. Then, the next time the patient is sitting, other intervals (i.e., delays) are tested, so that an optimal delay can be determined. Such a lookup table is preferably stored in the memory 94 of the implantable stimulation device 10. Table 600 is just one example of how the lookup table could be organized. Other variations are also within the spirit and scope of the present invention.

Figure 7:
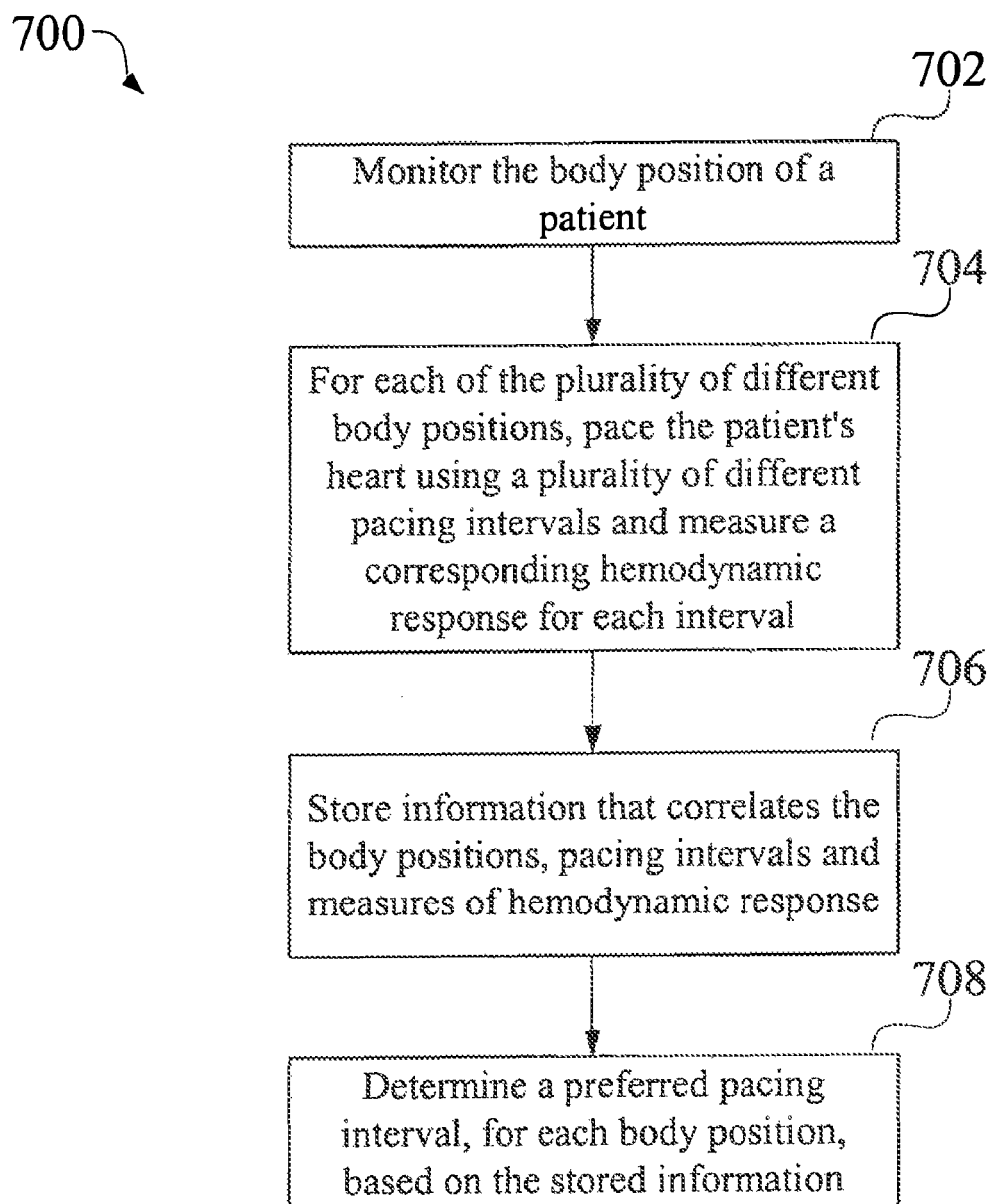
FIG. 7 is a high level flow diagram useful for describing how pacing interval optimization can be performed for various body positions, in accordance with embodiments of the present invention.

The high level flow diagram 700 shown in FIG. 7 will now be used to explain how automatic pacing interval optimization can be performed for various body positions, in accordance with embodiments of the present invention. The steps of flow diagram 700 are preferably performed by an implanted device, without any interaction from a physician or technician (i.e., without human interaction). As shown in FIG. 7, a patient's body position is monitored, at step 702, using a body position sensor, e.g., such as the ones described in U.S. Pat. No. 6,668,292, 6,466,821 or 6,625,493, which were incorporated by reference above. As explained in these patents, such sensors include accompanying software, firmware and/or hardware that can be implemented within the same implantable cardiac stimulation device (e.g., device 10) that is used for pacing. As mentioned above, the various body positions can include, but are not limited to, recumbent, sitting and standing.

As specified at step 704, for each of a plurality of different body positions, the patient's heart is paced using a plurality of different pacing intervals, and a corresponding hemodynamic response is measured for each pacing interval. The plurality of different pacing intervals used for pacing can be the same for each body position, or may differ for different body positions.

The information obtained at step 704 is stored (e.g., in memory 94 of stimulation device 10), as indicated at step 706. More specifically, step 706 includes storing information that correlates the body position, pacing intervals and measured hemodynamic responses. The information stored at step 706, is used at step 708, to select a preferred pacing interval (or preferred pacing intervals) for each body position. For example, the pacing interval producing the best hemodynamic response (relative or absolute) for a given body position, can be selected as the optimum pacing interval for that range. Alternatively, the stored information can be used to predict an optimum pacing interval for each body position (e.g., using a curve fitting algorithm, or the like).

Preferably, a plurality of test pacing intervals (e.g., a plurality of RV-LV delays) and corresponding hemodynamic response values are stored for each body position. By determining an optimum pacing interval from an ensemble of stored test intervals, greater accuracy and precision can be achieved. For example, a continuous curve can be fit to the stored data, as just mentioned. If the number of degrees of freedom of the curve is smaller than the number of test intervals, then effective averaging can be performed both at individual test intervals and across the range of test intervals. This approach is particularly desirable in optimization that occurs for different body positions, since body position changes with time. For these and other reasons, it is believed that embodiments of the present invention will provide better pacing interval optimization than is achieved by conventional gradient ascent techniques. More specifically, because the degree of expected variability and noise is high, it is believed that a gradient ascent technique for determining optimum pacing intervals would converge very slowly to optimum values.

One or more optimum pacing interval can be determined and stored for each body position. For example, as shown in FIG. 6, an optimum P-RV delay, RA-RV delay, and RV-LV delay can be stored for each body position. Optimum pacing intervals can be updated periodically, e.g., once a day, once every few hours, after a change in body position. In another embodiment, a new optimum pacing interval is determined each time a new hemodynamic response measure is stored. In a further embodiment, a new optimum pacing interval is determined after a new hemodynamic response measure has been determined for each of a predefined group of test intervals. Of course, other variations are also possible.

In accordance with an embodiment of the present invention, a previously determined optimum pacing interval is replaced with a new interval that corresponds to an improved hemodynamic response. In another embodiment, the new interval that corresponds to an improved hemodynamic response is used to form a running average with previously stored optimum pacing intervals. In still another embodiment, the new interval that corresponds to an improvement in hemodynamic response is combined with the previously stored value, e.g., using a weighted sum calculation. Of course, other variations are also possible.

As mentioned above, body position monitoring, pacing, measuring of hemodynamic response, and selection of preferred pacing intervals, in accordance with embodiments of the present invention, are preferably automatically performed by an implantable device without interaction from a physician or technician. Such systems provide pacing optimization less expensively than conventional devices that require human interaction, since physician or technician involvement is not necessary, and use of clinic time, space, and resources are avoided. Furthermore, embodiments of the present invention provide for frequent or semi-continuous optimization multiple times a day. In addition to being used to increase pacing optimization accuracy, embodiments of the present invention also track changes in underlying optimum pacing intervals that may occur with time and physiologic state.

Figure 8:
FIG. 8 shows an exemplary lookup table, according to another embodiment of the present invention that retains measures of cardiac performance for various combinations of heart rate ranges and body positions.

As mentioned above, data can be obtained and stored for various combinations of body positions and heart rate ranges. For example, FIG. 8 shows an exemplary portion of a lookup table 800, which retains cardiac performance measures for various combinations of heart rates ranges and body positions. For ease of illustration, table 800 is not populated with hemodynamic performance data.

In a manner similar to that described above with reference to FIG. 5, in accordance with an embodiment of the present invention, measures of cardiac performance for each of the plurality of different body positions are not made (and thus, there are no measures to store) when significant motion is detected. Alternatively, measures of cardiac performance are made, but are not stored (i.e., saved) when significant motion is detected. In accordance with a specific embodiment of the present invention, the previously determined optimal pacing parameter(s) is/are used for pacing, when significant motion is present, and test pacing intervals are not used until significant motion is not present. These features of the present invention reduce the likelihood that motion artifacts will corrupt measures of cardiac performance (i.e., hemodynamic response measurements), which are used to perform the pacing interval optimization calculations.

Pacing Interval Optimization for Various Levels of Autonomic Tone

Figure 9:
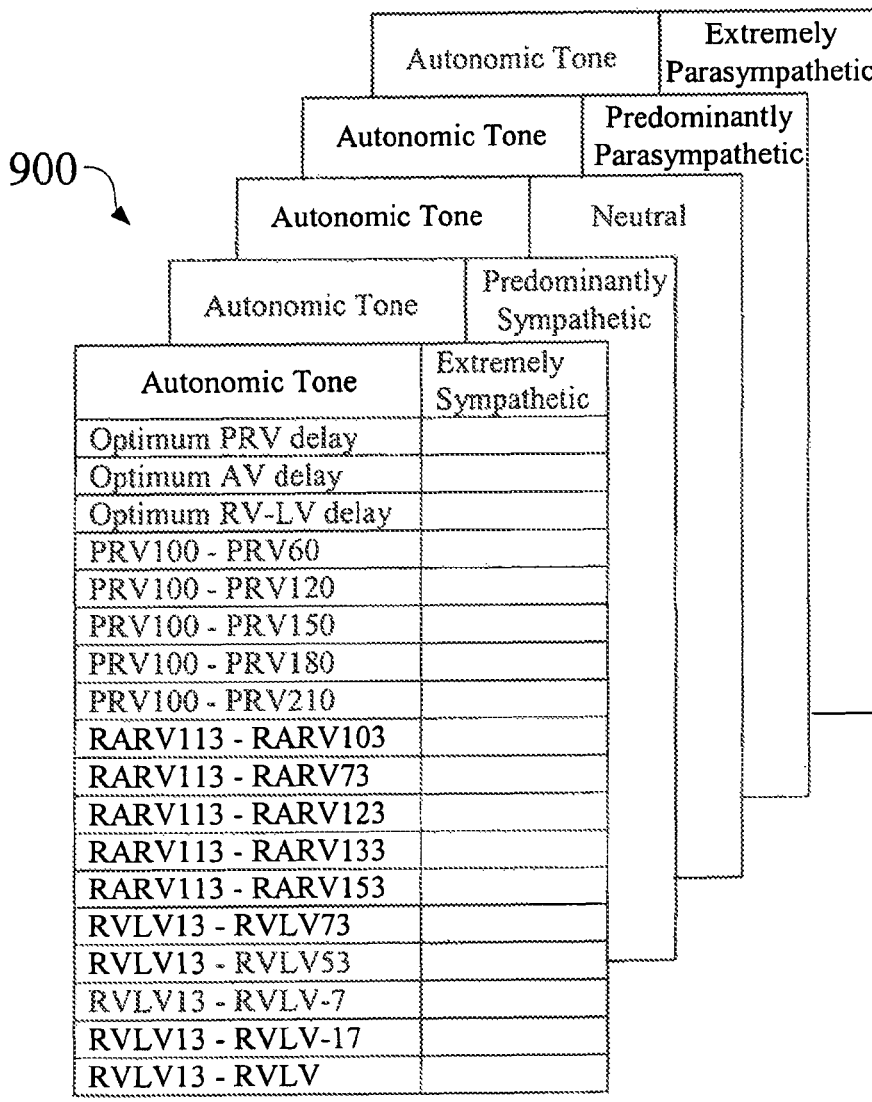
FIG. 9 shows an exemplary lookup table, according to another embodiment of the present invention that retains measures of cardiac performance for various levels of autonomic tone.

Embodiments of the present invention are also directed to determining and storing one or more optimum pacing interval (s) for each of a plurality of different levels of autonomic tone, as well as the data that is useful for determining such optimum interval(s). FIG. 9 shows an exemplary portion of a lookup table 900, which retains cardiac performance measures for different levels of autonomic tone. The different levels of autonomic tone can include, but are not limited to, extremely sympathetic, predominantly sympathetic, neutral, predominately parasympathetic and extremely parasympathetic.

Preferably, the autonomic tone of the patient is monitored using photo-plethysmography (PPG), as described in commonly invented and commonly owned U.S. patent application Ser. No. 10/764,419, entitled "Using Photo-Plethysmography to Monitor Autonomic Tone and Performing Pacing Optimization based on Monitored Autonomic Tone," filed Jan. 23, 2004, which is incorporated herein by reference. This can be accomplished, for example, by incorporating a light source and light detector into the same implantable stimulation device that is used for pacing, as is described in detail in the application just incorporated by reference, as well as in U.S. Pat. Nos. 6,591,639 and 6,40,675, which were incorporated by reference above. Changes in autonomic tone then can be monitored based on changes in pulse amplitude associated with a PPG signal that is produced using the light source and light detector. For example, this can include: recognizing an increase in pulse amplitude as a decrease in the sympathetic tone of the patient; recognizing an increase in pulse amplitude variability as a decrease in the sympathetic tone of the patient; recognizing a decrease in pulse amplitude as an increase in the sympathetic tone of the patient; and/or recognizing a decrease in pulse amplitude variability as an increase in the sympathetic tone of the patient. This may also include: recognizing an increase in pulse amplitude as an increase in the parasympathetic tone of the patient; recognizing an increase in pulse amplitude variability as an increase in the parasympathetic tone of the patient; recognizing a decrease in pulse amplitude as a decrease in the parasympathetic tone of the patient; and/or recognizing a decrease in pulse amplitude variability as a decrease in the parasympathetic tone of the patient. Various thresholds can be defined to distinguish between the different levels of autonomic tone, which as mentioned above, can include extremely sympathetic, predominantly sympathetic, neutral, predominately parasympathetic and extremely parasympathetic. Other schemes for monitoring autonomic tone, e.g., via the well-known technique of heart rate variability, are also within the spirit and scope of the present invention.

For ease of illustration, table 900 is not populated with hemodynamic performance data. As with tables 300 and 600, the data in table 900 can be collected during disjoint periods of time. For example, a person having an implanted stimulation device may have a predominantly parasympathetic autonomic tone while leisurely driving their car. In response to having to swerve to avoid an obstacle in the road, the person's autonomic tone may change to predominantly sympathetic or extremely sympathetic. Then, after the person has regained their composure, their autonomic tone may change to neutral or predominantly parasympathetic.

In accordance with an embodiment of the present invention, the hemodynamic response data that is used to perform pacing interval optimization is recorded in such a manner that the most recently obtained data can be combined with data from past and/or future times during which the patient has the same level of autonomic tone. For a more specific example, assume that during the time that the person is leisurely driving and has a predominantly parasympathetic autonomic tone, three different pacing intervals are tested, and the results (i.e., data) are stored. Then, when the person's autonomic tone returns to predominantly parasympathetic (following the swerving to avoid an obstacle incident), other intervals (i.e., delays) are tested, so that an optimal delay(s) can be determined for when the patient has a predominantly parasympathetic tone. Pacing intervals are also tested, and the results (i.e., data) are also stored, when the patients autonomic tone changed to predominantly sympathetic or extremely sympathetic, in response to having to swerve their car. Such data can then be used to determine an optimal delay(s) for when the patient has a predominantly sympathetic tone.

Table 900 is preferably stored in the memory 94 of the implantable stimulation device 10. Table 900 is just one example of how the lookup table could be organized. Other variations are also within the spirit and scope of the present invention. In accordance with embodiments of the present invention, lookup tables can retain cardiac performance measures for various combinations of levels of autonomic tone, heart rates ranges and/or body positions.

Figure 10:
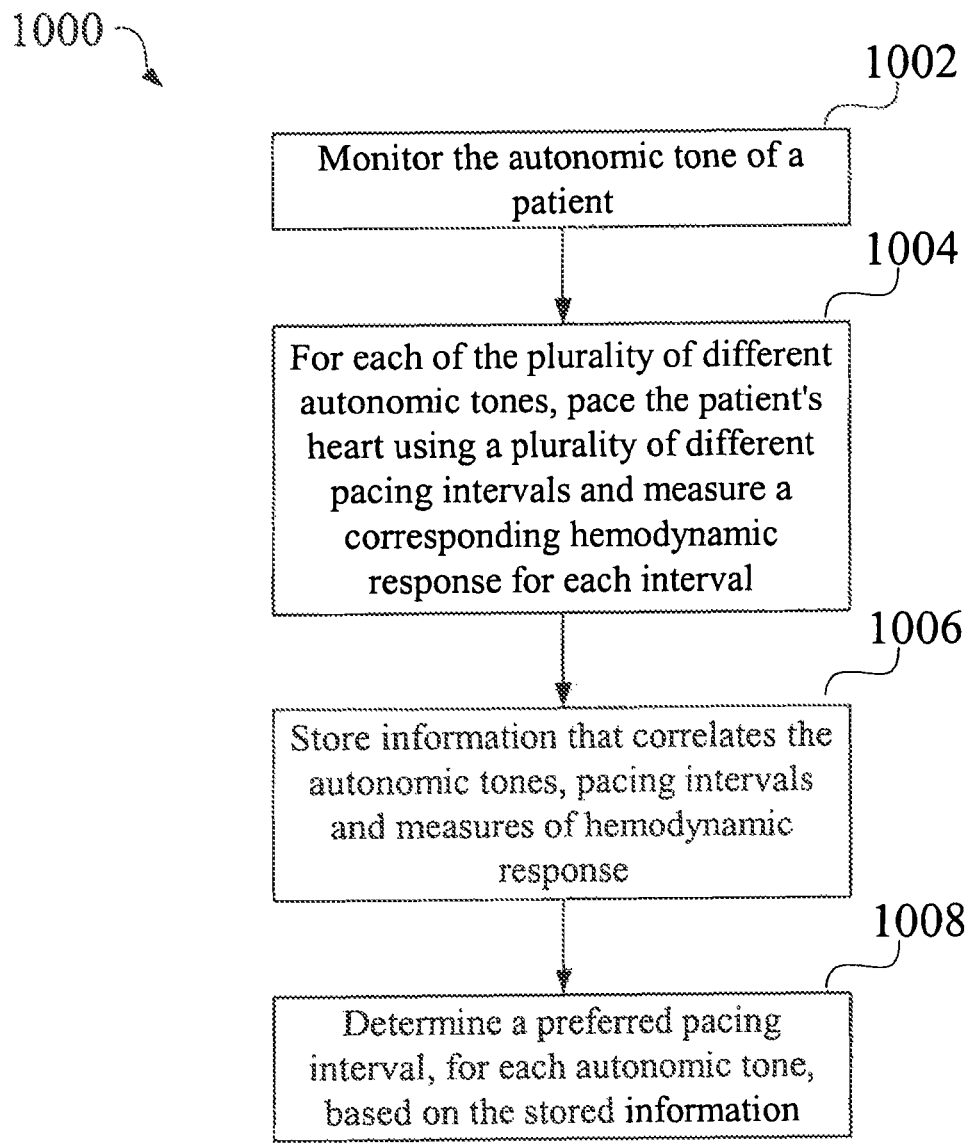
FIG. 10 is a high level flow diagram useful for describing how pacing interval optimization can be performed for various levels of autonomic tone, in accordance with embodiments of the present invention.

The high level flow diagram 1000 shown in FIG. 10 shows how automatic pacing interval optimization can be performed for various levels of autonomic tone in accordance with embodiments of the present invention. The steps of flow diagram 1000 are preferably performed by an implanted device, without any interaction from a physician or technician (i.e., without human interaction). As mentioned above, the various levels of autonomic tone can include, but are not limited to, extremely sympathetic, predominantly sympathetic, neutral, predominately parasympathetic and extremely parasympathetic. Details of the flow diagram 1000 are not discussed since details of similar flow diagrams were discussed above.

In a manner similar to that described above with reference to FIG. 5, in accordance with an embodiment of the present invention, measures of cardiac performance for each of the different levels of autonomic tone are not made (and thus, there are no measures to store) when significant motion is detected. Alternatively, measures of cardiac performance are made, but are not stored (i.e., saved) when significant motion is detected. In accordance with a specific embodiment of the present invention, the previously determined optimal pacing parameter(s) is/are used for pacing, when significant motion is present, and test pacing intervals are not used until significant motion is not present. These features of the present invention reduce the likelihood that motion artifacts will corrupt measures of cardiac performance (i.e., hemodynamic response measurements), which are used to perform the pacing interval optimization calculations.

Pacing Interval Optimization for Various Body Temperature Ranges

In the same way that a lookup table can be used to retain different optimum pacing interval settings for different heart rates, body positions and/or levels of autonomic tone, different optimum settings and raw data can also be retained for different body temperature ranges. The body temperature ranges can include, for example, 97.1-97.5, 97.6-98.0, 98.1-98.5, 98.6-99.0, etc. degrees Fahrenheit. An exemplary lookup table could look similar to those in the above discussed figures. In accordance with embodiments of the present invention, lookup tables can retain cardiac performance measures for various combinations of body temperature ranges, levels of autonomic tone, heart rates ranges and/or body positions.

Figure 11:
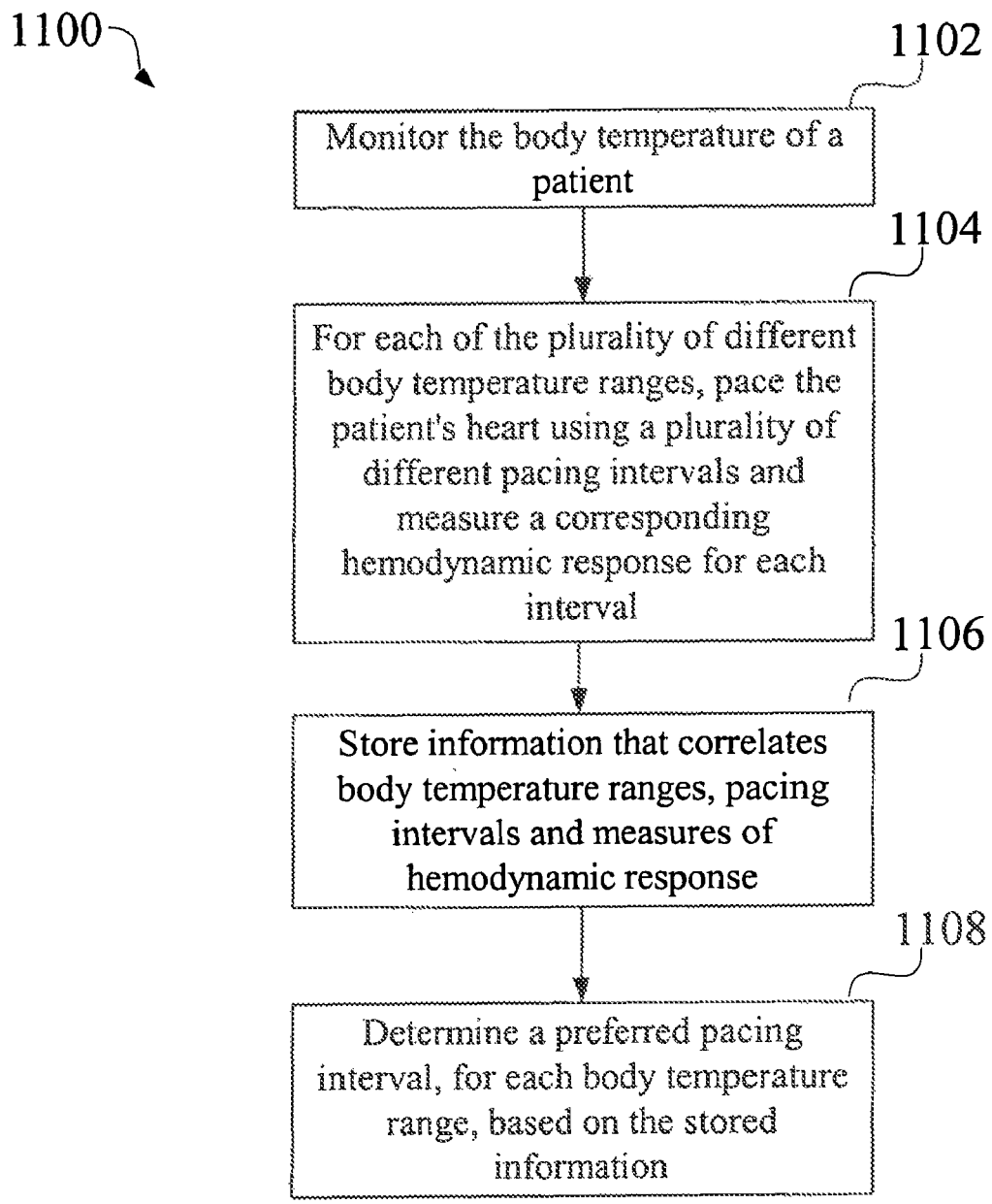
FIG. 11 is a high level flow diagram useful for describing how pacing interval optimization can be performed for various body temperature ranges, in accordance with embodiments of the present invention.

Preferably, the body temperature of the patient is monitored by incorporating a thermometer into the same implantable stimulation device that is used for pacing. The high level flow diagram 1100 shown in FIG. 11 shows how automatic pacing interval optimization can be performed for various body temperature ranges in accordance with embodiments of the present invention. The steps of flow diagram 1100 are preferably performed by an implanted device, without any interaction from a physician or technician (i.e., without human interaction). Details of the flow diagram 1100 are not discussed since details of similar flow diagrams were discussed above.

In a manner similar to that described above with reference to FIG. 5, in accordance with an embodiment of the present invention, measures of cardiac performance are not made (and thus, there are no measures to store) when significant motion is detected. Alternatively, measures of cardiac performance are made, but are not stored (i.e., saved) when significant motion is detected. In accordance with a specific embodiment of the present invention, the previously determined optimal pacing parameter(s) is/are used for pacing, when significant motion is present, and test pacing intervals are not used until significant motion is not present. These features of the present invention reduce the likelihood that motion artifacts will corrupt measures of cardiac performance (i.e., hemodynamic response measurements), which are used to perform the pacing interval optimization calculations.

Further Embodiments

Figure 12:
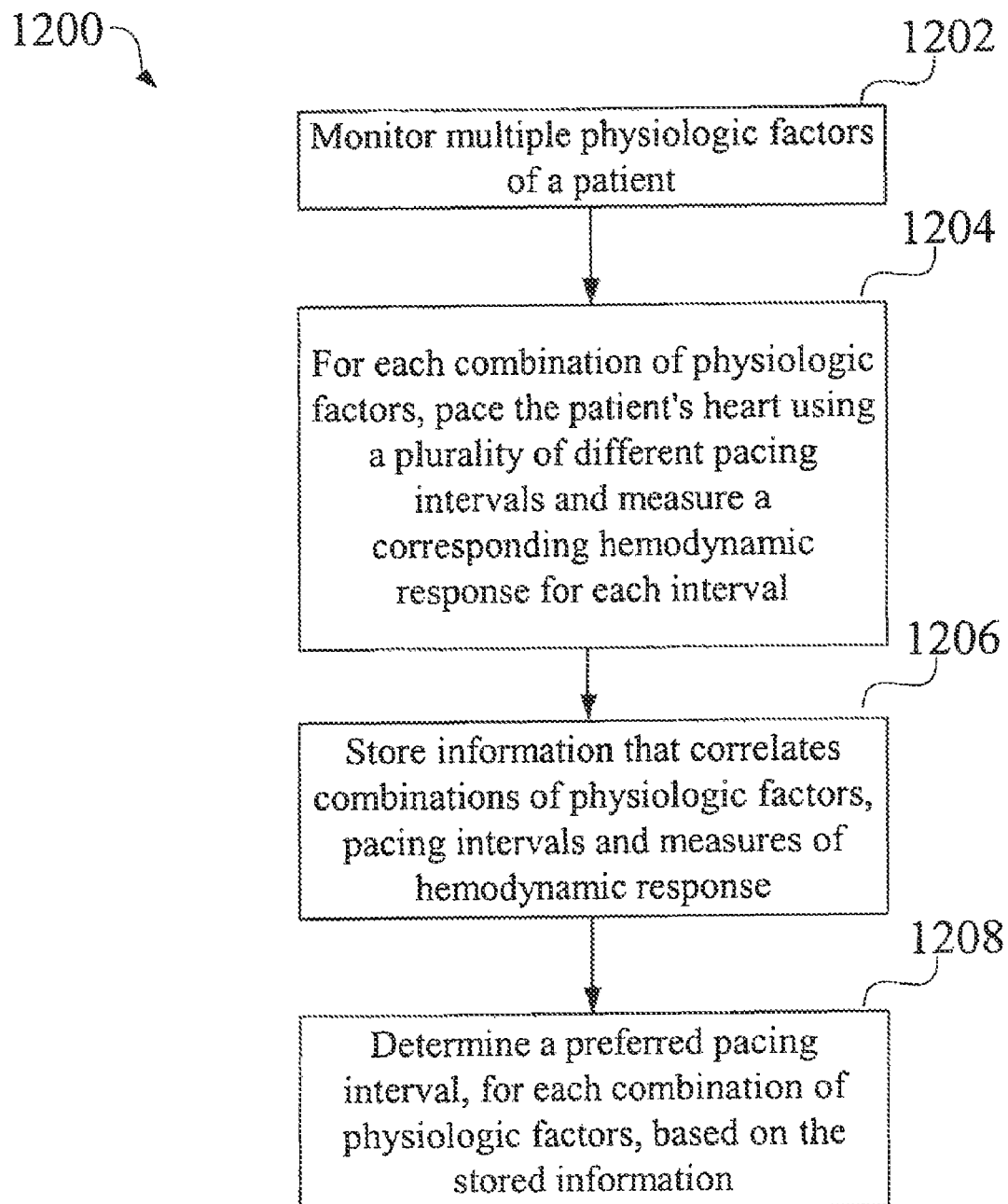
FIG. 12 is a high level flow diagram useful for describing how pacing interval optimization can be performed for various combinations of physiologic factors, in accordance with embodiments of the present invention.

The high level flow diagram 1200 shown in FIG. 12 shows how automatic pacing interval optimization can be performed for various combinations of physiologic factors. As mentioned above, such combinations can be combinations of body temperature ranges, levels of autonomic tone, heart rates ranges and/or body positions. The steps of flow diagram 1200 are preferably performed by an implanted device, without any interaction from a physician or technician (i.e., without human interaction).

As shown in FIG. 12, various physiologic factors are monitored, at step 1202. This can include, for example, monitoring heart rate, body position, autonomic tone and/or body temperature. As specified at step 1204, for each of a plurality of different combinations of physiologic factors, the patient's heart is paced using a plurality of different pacing intervals, and a corresponding hemodynamic response is measured for each pacing interval. The plurality of different pacing intervals used for pacing can be the same for each combination of physiologic factors, or may differ for different combinations.

The pacing intervals can define, e.g., atrioventricular (P-RV or RA-RV) delays. The pacing intervals can alternatively, or additionally, define, interventricular (RV-LV) delays, interatrial (RA-LA) delays, intraventricular $RV_1$-$RV_2$ or $LV_1$-$LV_2$) delays, etc. The initiating event, from which the interval/delay is specified, can be either a delivered pace pulse, or a sensed depolarization. The term P-RV delay is used herein to refer to a sensed atrial event and a paced ventricular event (P taken from its use in reference to atrial depolarization in standard ECG terminology). These are just a few examples, which are not meant to limit the scope of the present invention.

The information obtained at step 1204 is stored (e.g., in memory 94 of stimulation device 10), as indicated at step 1206. For example, step 1206 can include storing information that correlates any combination of heart rate, body position, autonomic tone and body temperature, along with pacing intervals and measured hemodynamic responses. The information stored at step 1206 is used at step 1208 to select a preferred pacing interval (or preferred pacing intervals) for each combination of physiologic factors. For example, the pacing interval producing the best hemodynamic response (relative or absolute) for a given heart rate range, body position, level of autonomic tone and body temperature range combination can be selected as the optimum pacing interval for that combination of physiologic factors. Alternatively, the stored information can be used to predict an optimum pacing interval for each combination (e.g., using a curve fitting algorithm, or the like).

Preferably, a plurality of test pacing intervals (e.g., a plurality of RV-LV delays) and corresponding hemodynamic response values are stored for each combination. By determining an optimum pacing interval from an ensemble of stored test intervals, greater accuracy and precision can be achieved. For example, a continuous curve can be fit to the stored data, as just mentioned. If the number of degrees of freedom of the curve is smaller than the number of test intervals, then effective averaging can be performed both at individual test intervals and across the range of test intervals. It is believed that embodiments of the present invention will provide better pacing interval optimization than is achieved by conventional gradient ascent techniques. More specifically, because the degree of expected variability and noise is high, it is believed that a gradient ascent technique for determining optimum pacing intervals would converge very slowly to optimum values.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention. Embodiments of the present invention can also be extended to types of physiologic factors other than those specifically mentioned above, as would be appreciated by one of ordinary skill in the art whom has read the above description.

What is claimed:

1. A method for performing automatic pacing interval optimization for each of a plurality of different body temperature ranges, comprising:
   (a) monitoring a patient's body temperature;
   (b) for each of the plurality of different body temperature ranges, pacing the patient's heart using a plurality of different pacing intervals and measuring a corresponding hemodynamic response for each interval;
   (c) storing information that correlates the body temperature ranges, pacing intervals and measures of hemodynamic response; and
   (d) determining at least one preferred pacing interval, for each body temperature range, based on the stored information;
   wherein steps (a) through (d) are performed by an implantable device without human interaction.

2. The method of claim 1, wherein step (d) includes periodically updating at least one preferred pacing interval for each body temperature range.

3. The method of claim 1, wherein step (d) includes updating at least one preferred pacing interval for at least one body temperature range, at least once per day.

4. The method of claim 1, wherein each time new information is stored for one of the body temperature ranges in step (c), step (d) includes updating at least one preferred pacing interval for that body temperature range.

5. The method of claim 1, wherein each time at least a predetermined amount of new information is stored for one of the body temperature ranges in step (c), step (d) includes updating at least one preferred pacing interval for that body temperature range.

6. The method of claim 1, wherein step (c) includes storing a plurality of measures of hemodynamic response for each pacing interval.

7. The method of claim 6, wherein the plurality of measures of hemodynamic response for each pacing interval includes a most recently determined measure of hemodynamic response and one or more previously determined measure of hemodynamic response.

8. The method of claim 1, wherein for at least one of the body temperature ranges, the pacing using the plurality of different pacing intervals occurs over noncontiguous periods of time.

9. The method of claim 1, wherein the stored measures of hemodynamic response are relative measures.

10. The method of claim 1, further comprising determining whether significant motion is present, and not performing at least at least one of steps (b) and (c) when significant motion is present.

11. The method of claim 10, wherein the determining whether significant motion is present includes comparing sensor measurements to a threshold.

12. The method of claim 10, wherein the determining whether significant motion is present includes examining a signal, used to produce the measures of hemodynamic response, for signs of motion.

13. An implantable system for performing automatic pacing interval optimization for each of a plurality of different body temperature ranges, comprising:
   means for monitoring a patient's body temperature;
   means for pacing the patient's heart using a plurality of different pacing intervals, for each of the plurality of different body temperature ranges;
   means for measuring hemodynamic response as the patient's heart is paced using the plurality of different pacing intervals, for each of the plurality of different body temperature ranges;
   means for storing information that correlates the body temperature ranges, pacing intervals and measures of hemodynamic response; and
   means for determining at least one preferred pacing interval, for each body temperature range, based on the stored information;
   wherein each said means performs its function without human interaction.

14. The system of claim 13, wherein at least one preferred pacing interval for each body temperature range is updated periodically.

15. The system of claim 13, wherein at least one preferred pacing interval for at least body temperature range, is updated at least once per day.

16. The system of claim 13, wherein each time new information is stored for one of the body temperature ranges, at least one preferred pacing, interval for that body temperature range is updated.

17. The system of claim 13, wherein each time at least a predetermined amount of new information is stored for one of the body temperature ranges, at least one preferred pacing interval for that body temperature range is updated.

18. The system of claim 13, wherein a plurality of measures of hemodynamic response are stored for each pacing interval.

19. The system of claim 18, wherein the plurality of measures of hemodynamic response for each pacing interval includes a most recently determined measure of hemodynamic response and one or more previously determined measure of hemodynamic response.

20. The system of claim 13, wherein for at least one of the body temperature ranges, the information is obtained and stored over noncontiguous periods of time.

21. The system of claim 13, wherein the stored measures of hemodynamic response are relative measures.

22. The system of claim 13, further comprising:
means for determining whether significant motion is present;
wherein said means for measuring hemodynamic response does not measure hemodynamic response when significant motion is present.

23. The system of claim 13, further comprising:
means for determining whether significant motion is present;
wherein said means for storing information does not store information that correlates the body temperature ranges, pacing intervals and measures of hemodynamic response, when significant motion is present.

24. The system of claim 23, wherein said means for measuring hernodynamic response includes a sensor; and wherein said means for monitoring motion includes said sensor.

25. The system of claim 23, wherein said means for measuring hemodynamic response includes a sensor that produces a signal that is used to produce measures of hemodynamic response; and wherein said signal is also examined for signs of motion.

* * * * *